(12) United States Patent
Rostami et al.

(10) Patent No.: US 10,455,863 B2
(45) Date of Patent: Oct. 29, 2019

(54) CARTRIDGE FOR ELECTRONIC VAPING DEVICE

(71) Applicant: Altria Client Services LLC, Richmond, VA (US)

(72) Inventors: Ali Rostami, Richmond, VA (US); Christopher S. Tucker, Midlothian, VA (US); David Kane, Richmond, VA (US); Peter Lipowicz, Midlothian, VA (US); Georgios Karles, Richmond, VA (US); Gerd Kobal, Sandy Hook, VA (US); Yezdi Pithawalla, Richmond, VA (US)

(73) Assignee: Altria Client Services LLC, Richmond, VA (US)

( * ) Notice: Subject to any disclaimer, the term of this patent is extended or adjusted under 35 U.S.C. 154(b) by 649 days.

(21) Appl. No.: 15/059,746

(22) Filed: Mar. 3, 2016

(65) Prior Publication Data

US 2017/0251721 A1 Sep. 7, 2017

(51) Int. Cl.
*H05B 1/02* (2006.01)
*A24F 47/00* (2006.01)
(Continued)

(52) U.S. Cl.
CPC .......... *A24F 47/008* (2013.01); *A61M 11/042* (2014.02); *A61M 15/0003* (2014.02);
(Continued)

(58) Field of Classification Search
CPC . A24F 47/008; A61M 1/042; A61M 15/0003; A61M 15/06; A61M 2016/0021;
(Continued)

(56) References Cited

U.S. PATENT DOCUMENTS 1,771,366 A 7/1930 Wyss
1,968,509 A 7/1934 Tiffany
(Continued)

FOREIGN PATENT DOCUMENTS

BE 421623 A 6/1937
CA 2947135 A1 11/2015
(Continued)

OTHER PUBLICATIONS

International Search Report and Written Opinion dated Jun. 8, 2017 issued in corresponding International Application No. PCT/EP2017/055472.
(Continued)

*Primary Examiner* — Mark H Paschall
(74) *Attorney, Agent, or Firm* — Harness, Dickey & Pierce, P.L.C.

(57) ABSTRACT

A cartridge for an e-vaping device enables separate vapors to be formed proximate to separate, respective ends of the cartridge. The cartridge includes multiple reservoirs and separate vaporizer assemblies coupled to separate reservoirs on opposite ends of the reservoirs. The separate reservoirs may hold separate pre-vapor formulations. The separate vaporizer assemblies may draw separate pre-vapor formulations from separate reservoirs towards opposite ends of the cartridge and vaporize the separate pre-vapor formulations via operation of separate heaters proximate to the separate ends. The separate heaters may be independently controlled to independently control vapor formation at the separate ends. The heaters may be controlled to independently control vapor formation rates proximate to the separate ends. The heaters may be controlled to form separate vapors at least one of simultaneously, concurrently, and at different times.

16 Claims, 2 Drawing Sheets

(51) Int. Cl.
 *A61M 15/06*  (2006.01)
 *A61M 11/04*  (2006.01)
 *A61M 15/00*  (2006.01)
 *A61M 16/00*  (2006.01)

(52) U.S. Cl.
 CPC ..... *A61M 15/06* (2013.01); *A61M 2016/0021* (2013.01); *A61M 2205/3368* (2013.01); *A61M 2205/8206* (2013.01)

(58) Field of Classification Search
 CPC .. A61M 2205/3368; A61M 2205/8206; H05B 1/02; H05B 1/0288
 USPC ........ 219/494, 497, 507, 483, 486; 392/395, 392/387
 See application file for complete search history.

(56) References Cited

U.S. PATENT DOCUMENTS

| | | | |
|---|---|---|---|
| 2,057,353 A | 10/1936 | Whittmore, Jr. | |
| 2,104,266 A | 1/1938 | McCormick | |
| 2,406,275 A | 8/1946 | Wejnarth | |
| 2,442,004 A | 5/1948 | Hayward-Butt | |
| 2,558,127 A | 6/1951 | Downs | |
| 2,642,313 A | 6/1953 | Montenier | |
| 2,728,981 A | 1/1956 | Hooper | |
| 2,830,597 A | 4/1958 | Kummli | |
| 2,907,686 A | 10/1959 | Siegel | |
| 2,971,039 A | 2/1961 | Westeren | |
| 2,972,557 A | 2/1961 | Toulmin, Jr. et al. | |
| 2,974,669 A | 3/1961 | Ellis | |
| 3,062,218 A | 11/1962 | Temkovits | |
| 3,200,819 A | 8/1965 | Gilbert | |
| 3,255,760 A | 6/1966 | Selke et al. | |
| 3,258,015 A | 6/1966 | Ellis et al. | |
| 3,356,094 A | 12/1967 | Ellis et al. | |
| 3,363,633 A | 1/1968 | Weber | |
| 3,402,723 A | 9/1968 | Hu | |
| 3,425,414 A | 2/1969 | La Roche | |
| 3,482,580 A | 12/1969 | Hollabaugh | |
| 3,633,881 A | 1/1972 | Yurdin | |
| 3,812,854 A | 5/1974 | Michaels et al. | |
| 3,878,041 A | 4/1975 | Leitnaker et al. | |
| 3,949,743 A | 4/1976 | Shanbrom | |
| 4,068,672 A | 1/1978 | Guerra | |
| 4,077,784 A | 3/1978 | Vayrynen | |
| 4,083,372 A | 4/1978 | Boden | |
| 4,131,119 A | 12/1978 | Blasutti | |
| 4,141,369 A | 2/1979 | Burruss | |
| 4,164,230 A | 8/1979 | Pearlman | |
| 4,193,411 A | 3/1980 | Faris et al. | |
| 4,219,032 A | 8/1980 | Tabatznik et al. | |
| 4,246,913 A | 1/1981 | Ogden et al. | |
| 4,257,389 A | 3/1981 | Texidor et al. | |
| 4,259,970 A | 4/1981 | Green, Jr. | |
| 4,413,641 A | 11/1983 | Dwyer, Jr. et al. | |
| 4,419,302 A | 12/1983 | Nishino et al. | |
| 4,629,604 A | 12/1986 | Spector | |
| 4,735,217 A | 4/1988 | Gerth et al. | |
| 4,765,347 A | 8/1988 | Sensabaugh, Jr. et al. | |
| 4,804,002 A | 2/1989 | Herron | |
| 4,846,199 A | 7/1989 | Rose | |
| 4,922,901 A | 5/1990 | Brooks et al. | |
| 4,945,929 A | 8/1990 | Egilmex | |
| 4,945,931 A | 8/1990 | Gori | |
| 4,947,874 A | 8/1990 | Brooks et al. | |
| 4,947,875 A | 8/1990 | Brooks et al. | |
| 4,961,727 A | 10/1990 | Beard | |
| 4,981,522 A | 1/1991 | Nichols et al. | |
| 4,991,606 A | 2/1991 | Serrano et al. | |
| 4,993,436 A | 2/1991 | Bloom, Jr. | |
| 5,016,656 A | 5/1991 | McMurtrie | |
| 5,040,552 A | 8/1991 | Schleich et al. | |
| 5,042,510 A | 8/1991 | Curtiss et al. | |
| 5,060,671 A | 10/1991 | Counts et al. | |
| 5,085,804 A | 2/1992 | Washburn | |
| 5,093,894 A | 3/1992 | Deevi et al. | |
| 5,095,921 A | 3/1992 | Losee et al. | |
| 5,139,594 A | 8/1992 | Rabin | |
| 5,144,962 A | 9/1992 | Counts et al. | |
| 5,159,940 A | 11/1992 | Hayward et al. | |
| 5,179,966 A | 1/1993 | Losee et al. | |
| 5,224,498 A | 7/1993 | Deevi et al. | |
| 5,228,460 A | 7/1993 | Sprinkel et al. | |
| 5,235,157 A | 8/1993 | Blackburn | |
| 5,249,586 A | 10/1993 | Morgan et al. | |
| 5,259,062 A | 11/1993 | Pelonis | |
| 5,269,327 A | 12/1993 | Counts et al. | |
| 5,322,075 A | 6/1994 | Deevi et al. | |
| 5,353,813 A | 10/1994 | Deevi et al. | |
| 5,369,723 A | 11/1994 | Counts et al. | |
| 5,388,594 A | 2/1995 | Counts et al. | |
| 5,396,911 A | 3/1995 | Casey, III et al. | |
| 5,404,871 A | 4/1995 | Goodman et al. | |
| 5,408,574 A | 4/1995 | Deevi et al. | |
| 5,498,855 A | 3/1996 | Deevi et al. | |
| 5,505,214 A | 4/1996 | Collins et al. | |
| 5,542,410 A | 8/1996 | Goodman et al. | |
| 5,591,368 A | 1/1997 | Fleischhauer et al. | |
| 5,613,504 A | 3/1997 | Collins et al. | |
| 5,665,262 A | 9/1997 | Hajaligol et al. | |
| 5,666,977 A | 9/1997 | Higgins et al. | |
| 5,666,978 A | 9/1997 | Counts et al. | |
| 5,692,095 A | 11/1997 | Young | |
| 5,743,251 A | 4/1998 | Howell et al. | |
| 5,797,390 A | 8/1998 | McSoley | |
| 5,865,185 A | 2/1999 | Collins et al. | |
| 5,878,752 A | 3/1999 | Adams et al. | |
| 5,894,841 A | 4/1999 | Voges | |
| 5,935,975 A | 8/1999 | Rose et al. | |
| 6,105,877 A | 8/2000 | Coffee | |
| 6,155,268 A | 12/2000 | Takeuchi | |
| 6,196,218 B1 | 3/2001 | Voges | |
| 6,234,167 B1 | 5/2001 | Cox et al. | |
| 6,386,674 B1 | 5/2002 | Corrigan, III et al. | |
| 6,443,146 B1 | 9/2002 | Voges | |
| 6,460,781 B1 | 10/2002 | Garcia et al. | |
| 6,501,052 B2 | 12/2002 | Cox et al. | |
| 6,516,796 B1 | 2/2003 | Cox et al. | |
| 6,532,965 B1 | 3/2003 | Abhulimen et al. | |
| 6,543,443 B1 | 4/2003 | Klimowicz et al. | |
| 6,568,390 B2 | 5/2003 | Nichols et al. | |
| 6,598,607 B2 | 7/2003 | Adiga et al. | |
| 6,663,019 B2 | 12/2003 | Garcia et al. | |
| 6,715,487 B2 | 4/2004 | Nichols et al. | |
| 6,715,697 B2 | 4/2004 | Duqueroie | |
| 6,772,756 B2 | 8/2004 | Shayan | |
| 6,799,576 B2 | 10/2004 | Farr | |
| 6,810,883 B2 | 11/2004 | Felter et al. | |
| 6,830,383 B2 | 12/2004 | Huang | |
| 6,854,470 B1 | 2/2005 | Pu | |
| 7,117,867 B2 | 10/2006 | Cox et al. | |
| 7,131,599 B2 | 11/2006 | Katase | |
| 7,167,641 B2 | 1/2007 | Tam et al. | |
| 7,173,222 B2 | 2/2007 | Cox et al. | |
| 7,195,403 B2 | 3/2007 | Oki et al. | |
| 7,281,670 B2 | 10/2007 | Lakatos et al. | |
| 7,445,484 B2 | 11/2008 | Wu | |
| 7,458,374 B2 | 12/2008 | Hale et al. | |
| D590,988 S | 4/2009 | Hon | |
| D590,989 S | 4/2009 | Hon | |
| D590,990 S | 4/2009 | Hon | |
| D590,991 S | 4/2009 | Hon | |
| 7,513,781 B2 | 4/2009 | Galauner et al. | |
| 7,540,286 B2 | 6/2009 | Cross et al. | |
| 7,614,402 B2 | 11/2009 | Gomes | |
| 7,726,320 B2 | 6/2010 | Robinson et al. | |
| 7,734,159 B2 | 6/2010 | Beland et al. | |
| 7,780,041 B2 | 8/2010 | Albisetti | |
| 7,832,410 B2 | 11/2010 | Hon | |
| 7,845,359 B2 | 12/2010 | Montaser | |
| 7,913,688 B2 | 3/2011 | Cross et al. | |
| 7,920,777 B2 | 4/2011 | Rabin et al. | |

(56) References Cited

U.S. PATENT DOCUMENTS

| | | |
|---|---|---|
| 7,997,280 B2 | 8/2011 | Rosenthal |
| 8,079,371 B2 | 12/2011 | Robinson et al. |
| D655,036 S | 2/2012 | Zhou |
| 8,127,772 B2 | 3/2012 | Montaser |
| 8,156,944 B2 | 4/2012 | Han |
| 8,205,622 B2 | 6/2012 | Pan |
| 8,258,192 B2 | 9/2012 | Wu et al. |
| 8,314,591 B2 | 11/2012 | Terry et al. |
| 8,320,751 B2 | 11/2012 | Porchia et al. |
| 8,349,251 B2 | 1/2013 | Woo et al. |
| 8,365,742 B2 | 2/2013 | Hon |
| 8,367,959 B2 | 2/2013 | Spertell |
| 8,371,310 B2 | 2/2013 | Brenneise |
| 8,375,957 B2 | 2/2013 | Hon |
| 8,393,331 B2 | 3/2013 | Hon |
| 8,402,976 B2 | 3/2013 | Fernando et al. |
| 8,449,766 B2 | 5/2013 | Feliers et al. |
| RE44,312 E | 6/2013 | Vieira |
| D684,311 S | 6/2013 | Liu |
| 8,459,270 B2 | 6/2013 | Coven et al. |
| 8,483,553 B2 | 7/2013 | Tollens et al. |
| 8,498,524 B2 | 7/2013 | Ruiz Ballesteros et al. |
| 8,499,766 B1 | 8/2013 | Newton |
| 8,511,318 B2 | 8/2013 | Hon |
| 8,528,569 B1 | 9/2013 | Newton |
| 8,550,068 B2 | 10/2013 | Terry et al. |
| 8,550,069 B2 | 10/2013 | Alelov |
| 8,584,670 B2 | 11/2013 | Hyde et al. |
| 8,689,804 B2 | 4/2014 | Fernando et al. |
| 8,689,805 B2 | 4/2014 | Hon |
| 8,833,364 B2 | 9/2014 | Buchberger |
| 8,915,254 B2 | 12/2014 | Monsees et al. |
| 8,944,052 B2 | 2/2015 | Osorio |
| 9,017,091 B2 | 4/2015 | Zhu et al. |
| 9,271,528 B2 | 3/2016 | Liu |
| 9,498,002 B1 | 11/2016 | Soreide |
| 9,603,386 B2 | 3/2017 | Xiang |
| 9,675,114 B2 | 6/2017 | Timmermans |
| 9,675,117 B2 | 6/2017 | Li et al. |
| 9,763,477 B2 | 9/2017 | Zhu |
| 9,808,032 B2 | 11/2017 | Yamada et al. |
| 9,888,714 B2 | 2/2018 | Cameron et al. |
| 9,974,743 B2 * | 5/2018 | Rose .................. A61K 9/12 |
| 10,015,986 B2 | 7/2018 | Cadieux et al. |
| 2002/0071871 A1 | 6/2002 | Snyder et al. |
| 2002/0078948 A1 | 6/2002 | Hindle et al. |
| 2002/0079309 A1 | 6/2002 | Cox et al. |
| 2002/0086852 A1 | 7/2002 | Cantor et al. |
| 2002/0146242 A1 | 10/2002 | Vieira |
| 2002/0170566 A1 | 11/2002 | Farr |
| 2002/0179102 A1 | 12/2002 | Farr |
| 2003/0056790 A1 | 3/2003 | Nichols et al. |
| 2003/0056791 A1 | 3/2003 | Nichols et al. |
| 2003/0075188 A1 | 4/2003 | Adiga et al. |
| 2003/0150451 A1 | 8/2003 | Shayan |
| 2004/0050396 A1 | 3/2004 | Squeo |
| 2004/0247301 A1 | 12/2004 | Yip et al. |
| 2005/0016550 A1 | 1/2005 | Katase |
| 2005/0150489 A1 | 7/2005 | Dunfield et al. |
| 2005/0235991 A1 | 10/2005 | Nichols et al. |
| 2005/0263618 A1 | 12/2005 | Spallek et al. |
| 2006/0054165 A1 | 3/2006 | Hughes et al. |
| 2006/0191546 A1 | 8/2006 | Takano et al. |
| 2006/0196518 A1 | 9/2006 | Hon |
| 2006/0213503 A1 | 9/2006 | Borgschulte et al. |
| 2007/0068523 A1 | 3/2007 | Fishman |
| 2007/0102013 A1 | 5/2007 | Adams et al. |
| 2007/0237499 A1 | 10/2007 | DeWitt et al. |
| 2007/0267031 A1 | 11/2007 | Hon |
| 2007/0267032 A1 | 11/2007 | Shan |
| 2008/0022999 A1 | 1/2008 | Belcastro et al. |
| 2008/0029084 A1 | 2/2008 | Costantino et al. |
| 2008/0138398 A1 | 6/2008 | Gonda |
| 2008/0138399 A1 | 6/2008 | Gonda |
| 2008/0230052 A1 | 9/2008 | Montaser |
| 2008/0241255 A1 | 10/2008 | Rose et al. |
| 2008/0247892 A1 | 10/2008 | Kawasumi |
| 2008/0276947 A1 | 11/2008 | Martzel |
| 2008/0299048 A1 | 12/2008 | Hale et al. |
| 2009/0056729 A1 | 3/2009 | Zawadzki et al. |
| 2009/0095287 A1 | 4/2009 | Emarlou |
| 2009/0095311 A1 | 4/2009 | Han |
| 2009/0095312 A1 | 4/2009 | Herbrich et al. |
| 2009/0126745 A1 | 5/2009 | Hon |
| 2009/0130216 A1 | 5/2009 | Cartt et al. |
| 2009/0151717 A1 | 6/2009 | Bowen et al. |
| 2009/0162294 A1 | 6/2009 | Werner |
| 2009/0188490 A1 | 7/2009 | Han |
| 2009/0230117 A1 | 9/2009 | Fernando et al. |
| 2009/0255534 A1 | 10/2009 | Paterno |
| 2009/0272379 A1 | 11/2009 | Thorens et al. |
| 2009/0283103 A1 | 11/2009 | Nielsen et al. |
| 2010/0020006 A1 | 1/2010 | Otani |
| 2010/0021900 A1 | 1/2010 | Gong et al. |
| 2010/0031968 A1 | 2/2010 | Sheikh et al. |
| 2010/0083959 A1 | 4/2010 | Siller |
| 2010/0126505 A1 | 5/2010 | Rinker |
| 2010/0200006 A1 | 8/2010 | Robinson et al. |
| 2010/0200008 A1 | 8/2010 | Taieb |
| 2010/0206317 A1 | 8/2010 | Albino et al. |
| 2010/0229881 A1 | 9/2010 | Hearn |
| 2010/0242975 A1 | 9/2010 | Hearn |
| 2010/0242976 A1 | 9/2010 | Katayama et al. |
| 2010/0266643 A1 | 10/2010 | Willett et al. |
| 2010/0307518 A1 | 12/2010 | Wang |
| 2011/0005535 A1 | 1/2011 | Xiu |
| 2011/0011396 A1 | 1/2011 | Fang |
| 2011/0036346 A1 | 2/2011 | Cohen et al. |
| 2011/0036363 A1 | 2/2011 | Urtsev et al. |
| 2011/0041858 A1 | 2/2011 | Montaser |
| 2011/0094523 A1 | 4/2011 | Thorens et al. |
| 2011/0120482 A1 | 5/2011 | Brenneise |
| 2011/0155153 A1 | 6/2011 | Thorens et al. |
| 2011/0168172 A1 | 7/2011 | Patton et al. |
| 2011/0209717 A1 | 9/2011 | Han |
| 2011/0226236 A1 | 9/2011 | Buchberger |
| 2011/0232654 A1 | 9/2011 | Mass |
| 2011/0245493 A1 | 10/2011 | Rabinowitz et al. |
| 2011/0265806 A1 | 11/2011 | Alarcon et al. |
| 2011/0277756 A1 | 11/2011 | Terry et al. |
| 2011/0277757 A1 | 11/2011 | Terry et al. |
| 2011/0277760 A1 | 11/2011 | Terry et al. |
| 2011/0277761 A1 | 11/2011 | Terry et al. |
| 2011/0277764 A1 | 11/2011 | Terry et al. |
| 2011/0277780 A1 | 11/2011 | Terry et al. |
| 2011/0290244 A1 | 12/2011 | Schennum |
| 2011/0303231 A1 | 12/2011 | Li et al. |
| 2011/0304282 A1 | 12/2011 | Li et al. |
| 2011/0315152 A1 | 12/2011 | Hearn et al. |
| 2012/0006342 A1 | 1/2012 | Rose et al. |
| 2012/0048266 A1 | 3/2012 | Alelov |
| 2012/0048466 A1 | 3/2012 | Eckert et al. |
| 2012/0111347 A1 | 5/2012 | Hon |
| 2012/0114809 A1 | 5/2012 | Edwards et al. |
| 2012/0118301 A1 | 5/2012 | Montaser |
| 2012/0145169 A1 | 6/2012 | Wu |
| 2012/0167906 A1 | 7/2012 | Gysland |
| 2012/0174914 A1 | 7/2012 | Pirshafiey et al. |
| 2012/0186594 A1 | 7/2012 | Liu |
| 2012/0199146 A1 | 8/2012 | Marangos |
| 2012/0199663 A1 | 8/2012 | Qiu |
| 2012/0207427 A1 | 8/2012 | Ito |
| 2012/0211015 A1 | 8/2012 | Li et al. |
| 2012/0230659 A1 | 9/2012 | Goodman et al. |
| 2012/0255567 A1 | 10/2012 | Rose et al. |
| 2012/0260927 A1 | 10/2012 | Liu |
| 2012/0285475 A1 | 11/2012 | Liu |
| 2012/0291791 A1 | 11/2012 | Pradeep |
| 2012/0312313 A1 | 12/2012 | Frija |
| 2012/0318882 A1 | 12/2012 | Abehasera |
| 2013/0014772 A1 | 1/2013 | Liu |
| 2013/0019887 A1 | 1/2013 | Liu |
| 2013/0025609 A1 | 1/2013 | Liu |
| 2013/0037041 A1 | 2/2013 | Worm et al. |

(56) References Cited

U.S. PATENT DOCUMENTS

| | | |
|---|---|---|
| 2013/0042865 A1 | 2/2013 | Monsees et al. |
| 2013/0056013 A1 | 3/2013 | Terry et al. |
| 2013/0074854 A1 | 3/2013 | Lipowicz |
| 2013/0152956 A1 | 6/2013 | von Borstel et al. |
| 2013/0192615 A1 | 8/2013 | Tucker et al. |
| 2013/0192616 A1 | 8/2013 | Tucker et al. |
| 2013/0192619 A1 | 8/2013 | Tucker et al. |
| 2013/0192620 A1 | 8/2013 | Tucker et al. |
| 2013/0192621 A1 | 8/2013 | Li et al. |
| 2013/0192622 A1 | 8/2013 | Tucker et al. |
| 2013/0192623 A1 | 8/2013 | Tucker et al. |
| 2013/0213418 A1 | 8/2013 | Tucker et al. |
| 2013/0213419 A1 | 8/2013 | Tucker et al. |
| 2013/0220315 A1 | 8/2013 | Conley et al. |
| 2013/0228191 A1 | 9/2013 | Newton |
| 2013/0284192 A1 | 10/2013 | Peleg et al. |
| 2013/0298905 A1 | 11/2013 | Levin et al. |
| 2013/0312778 A1 | 11/2013 | Shibuichi |
| 2013/0319407 A1 | 12/2013 | Liu |
| 2013/0319440 A1 | 12/2013 | Capuano |
| 2013/0340775 A1 | 12/2013 | Juster et al. |
| 2014/0000638 A1 | 1/2014 | Sebastian et al. |
| 2014/0014125 A1 | 1/2014 | Fernando et al. |
| 2014/0060527 A1 | 3/2014 | Liu |
| 2014/0060556 A1 | 3/2014 | Liu |
| 2014/0081234 A1 | 3/2014 | Eggert et al. |
| 2014/0096782 A1 | 4/2014 | Ampolini et al. |
| 2014/0123989 A1 | 5/2014 | LaMothe |
| 2014/0153195 A1 | 6/2014 | You et al. |
| 2014/0163048 A1 | 6/2014 | Barker et al. |
| 2014/0166029 A1 | 6/2014 | Weigensberg et al. |
| 2014/0174441 A1 | 6/2014 | Seeney et al. |
| 2014/0190496 A1 | 7/2014 | Wensley et al. |
| 2014/0202474 A1 | 7/2014 | Peleg et al. |
| 2014/0209105 A1 | 7/2014 | Sears et al. |
| 2014/0224245 A1 | 8/2014 | Alelov |
| 2014/0246035 A1 | 9/2014 | Minskoff et al. |
| 2014/0261486 A1 | 9/2014 | Potter et al. |
| 2014/0261488 A1 | 9/2014 | Tucker |
| 2014/0261492 A1 | 9/2014 | Kane et al. |
| 2014/0261788 A1 | 9/2014 | Lewis et al. |
| 2014/0267488 A1 | 9/2014 | Ready et al. |
| 2014/0366898 A1* | 12/2014 | Monsees ............... A24F 47/008 131/329 |
| 2015/0020823 A1 | 1/2015 | Lipowicz et al. |
| 2015/0027454 A1 | 1/2015 | Li et al. |
| 2015/0027468 A1 | 1/2015 | Li et al. |
| 2015/0027469 A1 | 1/2015 | Tucker et al. |
| 2015/0027470 A1 | 1/2015 | Kane et al. |
| 2015/0047662 A1* | 2/2015 | Hopps ................... A24F 47/008 131/329 |
| 2015/0068544 A1 | 3/2015 | Moldoveanu et al. |
| 2015/0164141 A1 | 6/2015 | Newton |
| 2015/0196059 A1 | 7/2015 | Liu |
| 2015/0258289 A1 | 9/2015 | Henry, Jr. et al. |
| 2015/0313275 A1 | 11/2015 | Anderson et al. |
| 2015/0320116 A1 | 11/2015 | Bleloch et al. |
| 2015/0335070 A1 | 11/2015 | Sears et al. |
| 2015/0351456 A1 | 12/2015 | Johnson et al. |
| 2016/0021930 A1 | 1/2016 | Minskoff et al. |
| 2016/0109115 A1 | 4/2016 | Lipowicz |
| 2016/0120224 A1 | 5/2016 | Mishra et al. |
| 2016/0135506 A1 | 5/2016 | Sanchez et al. |
| 2016/0174611 A1 | 6/2016 | Monsees et al. |
| 2016/0183598 A1 | 6/2016 | Tucker et al. |
| 2016/0192708 A1* | 7/2016 | DeMeritt ................. H05B 3/40 131/329 |
| 2016/0235123 A1 | 8/2016 | Krietzman |
| 2016/0331026 A1 | 11/2016 | Cameron |
| 2016/0334119 A1* | 11/2016 | Cameron ................. F24F 3/16 |
| 2017/0027232 A1 | 2/2017 | Scheck et al. |
| 2017/0042251 A1 | 2/2017 | Yamada et al. |
| 2017/0086500 A1 | 3/2017 | Li et al. |
| 2017/0109877 A1 | 4/2017 | Peleg et al. |
| 2017/0112197 A1 | 4/2017 | Li et al. |
| 2017/0150755 A1 | 6/2017 | Batista |
| 2017/0150758 A1 | 6/2017 | Fernando et al. |
| 2017/0157341 A1* | 6/2017 | Pandya ................. A61M 11/007 |
| 2017/0290998 A1 | 10/2017 | Poston et al. |
| 2017/0354180 A1* | 12/2017 | Fornarelli ............. A24F 47/008 |
| 2018/0007966 A1 | 1/2018 | Li et al. |
| 2018/0235277 A1 | 8/2018 | Lin et al. |

FOREIGN PATENT DOCUMENTS

| | | |
|---|---|---|
| CH | 421786 A | 9/1966 |
| CN | 87104459 A | 2/1988 |
| CN | 2719043 Y | 8/2005 |
| CN | 2777995 Y | 5/2006 |
| CN | 101084801 A | 12/2007 |
| CN | 101116542 A | 2/2008 |
| CN | 201018927 Y | 2/2008 |
| CN | 201029436 Y | 3/2008 |
| CN | 201054977 Y | 5/2008 |
| CN | 201067079 Y | 6/2008 |
| CN | 201076006 Y | 6/2008 |
| CN | 201085044 Y | 7/2008 |
| CN | 101518361 A | 9/2009 |
| CN | 201379072 Y | 1/2010 |
| CN | 201709398 U | 1/2011 |
| CN | 201789924 U | 4/2011 |
| CN | 201797997 U | 4/2011 |
| CN | 102106611 A | 6/2011 |
| CN | 201860753 U | 6/2011 |
| CN | 102166044 A | 8/2011 |
| CN | 202014571 | 10/2011 |
| CN | 202014572 U | 10/2011 |
| CN | 202026804 U | 11/2011 |
| CN | 202233005 U | 5/2012 |
| CN | 202233007 U | 5/2012 |
| CN | 102655773 A | 9/2012 |
| DE | 2653133 A1 | 5/1978 |
| DE | 3640917 A1 | 8/1988 |
| DE | 3735704 A1 | 5/1989 |
| DE | 19854009 A1 | 5/2000 |
| EP | 0893071 A1 | 7/1908 |
| EP | 0277519 A2 | 8/1988 |
| EP | 0295122 A2 | 12/1988 |
| EP | 0358 002 A2 | 3/1990 |
| EP | 0358002 A2 | 3/1990 |
| EP | 0358114 A2 | 3/1990 |
| EP | 0430566 A2 | 6/1991 |
| EP | 0845220 A1 | 6/1998 |
| EP | 0857431 A1 | 8/1998 |
| EP | 1989946 | 11/2008 |
| EP | 2022350 A1 | 2/2009 |
| EP | 2113178 A1 | 11/2009 |
| EP | 2454956 A1 | 5/2012 |
| EP | 2460424 A1 | 6/2012 |
| EP | 2481308 A1 | 8/2012 |
| EP | 2671461 A1 | 12/2013 |
| GB | 680815 A | 10/1952 |
| GB | 2148079 A | 5/1985 |
| GB | 2513631 A | 11/2014 |
| GB | 2524779 A | 10/2015 |
| JP | 61068061 A | 4/1986 |
| JP | 2006320286 A | 11/2006 |
| KR | 100636287 B1 | 10/2006 |
| NL | 8201585 A | 11/1982 |
| WO | WO-86/02528 A1 | 5/1986 |
| WO | WO-9003224 A1 | 4/1990 |
| WO | WO-95/02970 A1 | 2/1995 |
| WO | WO-1997/042993 A2 | 11/1997 |
| WO | WO-00/28843 A1 | 5/2000 |
| WO | WO-03037412 A2 | 5/2003 |
| WO | WO-2004/080216 A1 | 9/2004 |
| WO | WO-2004/095955 A1 | 11/2004 |
| WO | WO-2005/053444 A1 | 6/2005 |
| WO | WO-2005/099494 A1 | 10/2005 |
| WO | WO-2007/066374 A1 | 6/2007 |
| WO | WO-2007/078273 A1 | 7/2007 |
| WO | WO-2007/098337 A2 | 8/2007 |
| WO | WO-2007/131449 A1 | 11/2007 |
| WO | WO-2007/131450 A1 | 11/2007 |

(56) References Cited

FOREIGN PATENT DOCUMENTS

| | | |
|---|---|---|
| WO | WO-2007/141668 A2 | 12/2007 |
| WO | WO-2008/055423 A1 | 5/2008 |
| WO | WO-2010/091593 A1 | 8/2010 |
| WO | WO-2010/145468 A1 | 12/2010 |
| WO | WO-2011/124033 A1 | 10/2011 |
| WO | WO-2011/125058 A1 | 10/2011 |
| WO | WO-2011/146372 A2 | 11/2011 |
| WO | WO-2012/129787 A1 | 10/2012 |
| WO | WO-2012/129812 A1 | 10/2012 |
| WO | WO-2012/142293 A2 | 10/2012 |
| WO | WO-2012/174677 A1 | 12/2012 |
| WO | WO-2013/022936 A1 | 2/2013 |
| WO | WO-2013/027249 A1 | 2/2013 |
| WO | WO-2013116558 | 8/2013 |
| WO | WO-2014110119 A1 | 7/2014 |
| WO | WO-2014187770 A2 | 11/2014 |
| WO | WO-2015/040180 A2 | 3/2015 |
| WO | WO-2015/079197 A1 | 6/2015 |
| WO | WO-2015150699 A1 | 10/2015 |
| WO | WO-2016005602 A1 | 1/2016 |
| WO | WO-2016015246 A1 | 2/2016 |
| WO | WO-2016183573 A1 | 11/2016 |

OTHER PUBLICATIONS

International Search Report and Written Opinion dated May 24, 2017 issued in corresponding International Application No. PCT/EP2017/055734.
Non-Final Office Action dated Sep. 28, 2018 in U.S. Appl. No. 15/059,790.
Communication Pursuant to Rule 114(2) dated Oct. 1, 2018 in European Application No. 17710247.2.
International Search Report and Written Opinion for PCT/EP2017/055733 dated Jun. 21, 2017.
Invitation to Pay Additional Fees for PCT/EP2017/055098 dated May 10, 2017.
International Search Report and Written Opinion for PCT/EP2017/055098 dated Jul. 14, 2017.
International Search Report and Written Opinion for PCT/EP2017/055100 dated Jun. 19, 2017.
Office Action for corresponding Russian Application No. 2015144179 dated Jul. 11, 2017 and English translation thereof.
U.S. Office Action issued in co-pending U.S. Appl. No. 15/067,990 dated Mar. 19, 2018.
U.S. Office Action issued in co-pending U.S. Appl. No. 15/059,791 dated Mar. 21, 2018.
U.S. Office Action issued in co-pending U.S. Appl. No. 15/059,790 dated Mar. 21, 2018.
U.S. Office Action issued in co-pending U.S. Appl. No. 15/063,900 dated Apr. 24, 2018.
U.S. Office Action issued in co-pending U.S. Appl. No. 15/067,810 dated Jun. 29, 2018.
U.S. Office Action issued in co-pending U.S. Appl. No. 15/067,867 dated Aug. 3, 2018.
International Search Report and Written Opinion for PCT/US2013/027424 dated Apr. 25, 2013.
Lee et al., Technique for aerosol generation with controllable micrometer size distribution, Chemosphere 73 (2008), pp. 760-767.
International Preliminary Report on Patentability for PCT/US2013/027424 dated Sep. 4, 2014.
International Search Report and Written Opinion for PCT/US2013/022330 dated Jul. 15, 2014.
International Search Report dated Jul. 15, 2014.
Moroccan Examination Report Application No. 38386 dated Mar. 18, 2016.
Moroccan Notification of a Preliminary Search Report with Opinion on Patentability on Application No. 38386 dated Dec. 23, 2015.
Chinese Office Action dated Apr. 1, 2017 issued in corresponding Chinese Patent Application No. 201480016196.1 (with translation).
Intlnernational Search Report and Written Opinion dated May 9, 2017 issued in corresponding PCT Application No. PCT/EP2017/055102.
International Search Report and Written Opinion for PCT/EP2017/055725 dated Jun. 13, 2017.
Notice of Allowance dated Apr. 23, 2019 for corresponding U.S. Appl. No. 15/059,791.
U.S. Office Action dated Nov. 9, 2018 issued in co-pending U.S. Appl. No. 15/059,791.
U.S. Office Action dated Nov. 16, 2018 issued in co-pending U.S. Appl. No. 15/067,990.
U.S. Office Action dated Mar. 21, 2019 issued in co-pending U.S. Appl. No. 15/059,790.
U.S. Office Action dated Sep. 28, 2018 issued in co-pending U.S. Appl. No. 15/059,790.
International Search Report and Written Opinion thereof dated May 10, 2017 issued in International Application No. PCT/EP2017/055098.
U.S. Office Action for corresponding U.S. Appl. No. 14/199,365 dated Jun. 20, 2016.
U.S. Office Action dated Apr. 5, 2019 for corresponding U.S. Appl. No. 15/067,990.
Kazakhstan Notice of Allowance dated Apr. 11, 2019 for corresponding Kazakhstan Application No. 2018/00693.1.
U.S. Notice of Allowance dated May 2, 2019 for corresponding U.S. Appl. No. 15/067,867.
U.S. Notice of Allowance dated May 7, 2019 for corresponding U.S. Appl. No. 15/067,810.
U.S. Notice of Allowance dated Apr. 23, 2019 for corresponding U.S. Appl. No. 15/059,791.
U.S. Notice of Allowance dated May 16, 2019 for corresponding U.S. Appl. No. 15/063,900.
U.S. Notice of Allowance dated Aug. 14, 2019 for corresponding U.S. Appl. No. 15/059,791.

* cited by examiner

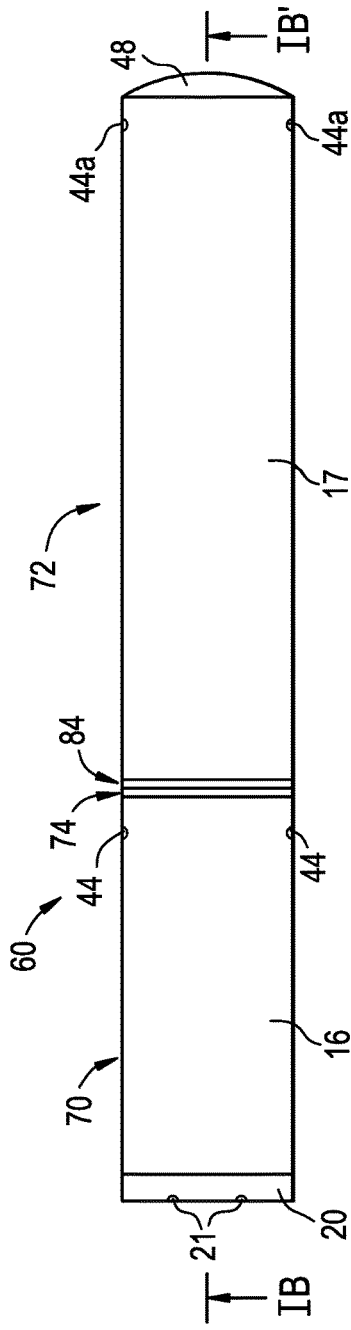
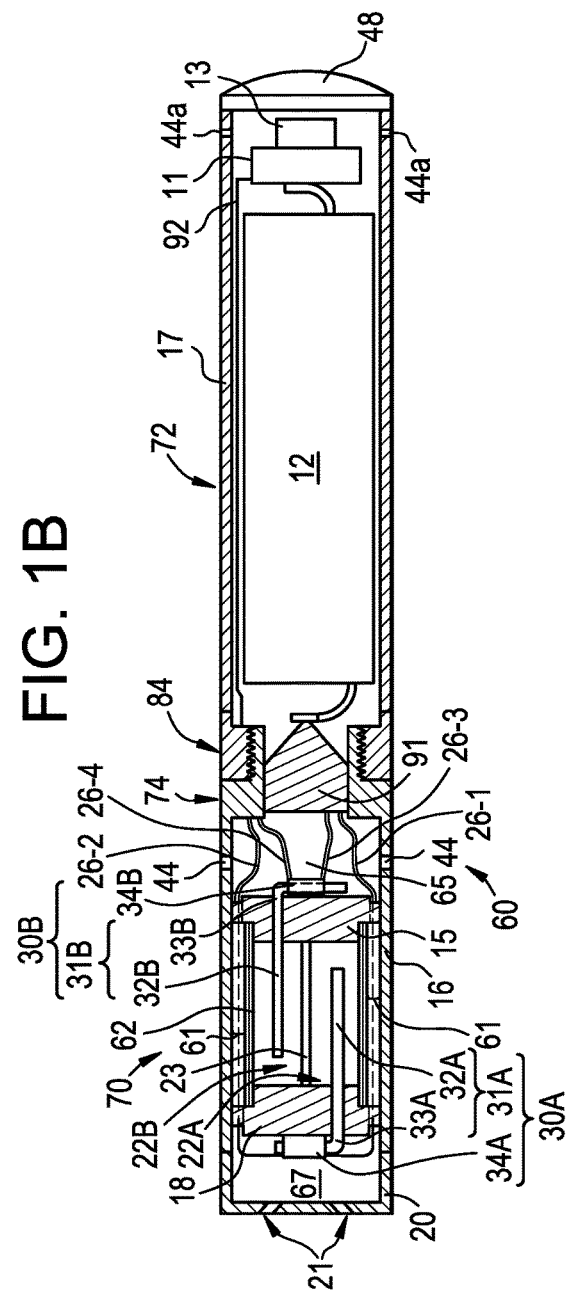

CARTRIDGE FOR ELECTRONIC VAPING DEVICE

BACKGROUND

Field

Example embodiments relate to electronic vaping or e-vaping devices.

Description of Related Art

E-vaping devices, also referred to herein as electronic vaping devices (EVDs) may be used by adult vapors for portable vaping. An e-vaping device may vaporize a pre-vapor formulation to form a vapor. The e-vaping device may include a reservoir that holds a pre-vapor formulation and a heater that vaporizes the pre-vapor formulation.

In some cases, an e-vaping device may include multiple pre-vapor formulations. However, in some cases the separate pre-vapor formulations may react with each other when held in a reservoir of an e-vaping device. Such reactions may result in the degradation of one or more of the pre-vapor formulations, formation of one or more reaction products, thereby reducing a shelf-life of a portion of the e-vaping device.

SUMMARY

According to some example embodiments, a cartridge for an e-vaping device may include a housing, at least first and second reservoirs positioned within the housing, and at least first and second vaporizer assemblies positioned within the housing on opposite ends of the first and second reservoirs. The housing may include first and second ends. The first and second reservoirs may be positioned within the housing between the first and second ends. The first and second reservoirs may be configured to hold respective first and second pre-vapor formulations. The first and second vaporizer assemblies may be positioned within the housing on opposite ends of the first and second reservoirs. The first vaporizer assembly may be coupled to the first reservoir. The first vaporizer assembly may be configured to vaporize the first pre-vapor formulation to generate a first vapor closer to the first end than the second end. The second vaporizer assembly may be coupled to the second reservoir. The second vaporizer assembly may be configured to vaporize the second pre-vapor formulation to generate a second vapor closer to the second end than the first end.

in some example embodiments, the first vaporizer assembly may include a first dispensing interface configured to draw the first pre-vapor formulation from the first reservoir and a first heater coupled to the first dispensing interface. The first heater may be configured to vaporize the drawn first pre-vapor formulation. The second vaporizer assembly may include a second dispensing interface configured to draw the second pre-vapor formulation from the second reservoir and a second heater coupled to the second dispensing interface. The second heater may be configured to vaporize the drawn second pre-vapor formulation.

In some example embodiments, the first dispensing interface may include a porous material arranged in fluidic communication with the first heater.

In some example embodiments, the porous material may be a wick having an elongated form and arranged in fluidic communication with the first reservoir.

In some example embodiments, the wick may extend at least partially through the first heater.

In some example embodiments, the first and second vaporizer assemblies may be configured to generate the first and second vapors at different rates.

In some example embodiments, the first and second vaporizer assemblies may be configured to generate the first and second vapors at different times.

According to some example embodiments, an e-vaping device may include a cartridge and a power supply section. The cartridge may include a housing, at least first and second reservoirs positioned within the housing, and at least first and second vaporizer assemblies positioned within the housing on opposite ends of the first and second reservoirs. The housing may include first and second ends. The first and second reservoirs may be positioned within the housing between the first and second ends. The first and second reservoirs may be configured to hold respective first and second pre-vapor formulations. The first and second vaporizer assemblies may be positioned within the housing on opposite ends of the first and second reservoirs. The first vaporizer assembly may be coupled to the first reservoir. The first vaporizer assembly may be configured to vaporize the first pre-vapor formulation to generate a first vapor closer to the first end than the second end. The second vaporizer assembly may be coupled to the second reservoir. The second vaporizer assembly may be configured to vaporize the second pre-vapor formulation to generate a second vapor closer to the second end than the first end. The power supply section may be configured to selectively supply power to the first and second vaporizer assemblies.

In some example embodiments, the power supply section may further include control circuitry, the control circuitry being configured to independently control vapor generation by the first and second vaporizer assemblies.

In some example embodiments, the control circuitry may be configured to independently control vapor generation by the first and second vaporizer assemblies based on independently controlling power supplied to the first and second vaporizer assemblies.

In some example embodiments, the control circuitry may be further configured to cause the first and second vaporizer assemblies to generate the first vapor and the second vapor at different times, based on independently controlling the first and second vaporizer assemblies.

In some example embodiments, the control circuitry may be configured to activate a first heater included in the first vaporizer assembly, such that a viscosity of the second pre-vapor formulation is reduced, prior to controlling the second vaporizer assembly to vaporize the second pre-vapor formulation.

In some example embodiments, the first vaporizer assembly may include a first dispensing interface configured to draw the first pre-vapor formulation from the first reservoir and a first heater coupled to the first dispensing interface. The first heater may be configured to vaporize the drawn first pre-vapor formulation. The second vaporizer assembly may include a second dispensing interface configured to draw the second pre-vapor formulation from the second reservoir and a second heater coupled to the second dispensing interface. The second heater may be configured to vaporize the drawn second pre-vapor formulation.

In some example embodiments, the first dispensing interface may include a porous material, the porous material being arranged in fluidic communication with the first heater.

In some example embodiments, the porous material may be a wick having an elongated form and arranged in fluidic communication with the first reservoir.

In some example embodiments, the power supply section may include a rechargeable battery, the power supply section being removably coupled to the cartridge.

According to some example embodiments, a method may include configuring a cartridge to generate separate vapors at separate ends of an enclosure. The configuring may include positioning at least first and second reservoirs in a housing, such that the first and second reservoirs are positioned between first and second ends of the housing, the first and second reservoirs being configured to hold respective first and second pre-vapor formulations. The configuring may include coupling at least first and second vaporizer assemblies to opposite ends of the first and second reservoirs, such that the first vaporizer assembly is configured to vaporize the first pre-vapor formulation to generate a first vapor closer to the first end than the second end, and the second vaporizer assembly is configured to vaporize the second pre-vapor formulation to generate a second vapor closer to the second end than the first end.

In some example embodiments, the method may include coupling the cartridge to a power supply section, such that the power supply section is configured to selectively supply power to the first and second vaporizer assemblies.

In some example embodiments, the power supply section may include control circuitry, the control circuitry being configured to control power supplied from the power supply section, such that coupling the cartridge to the power supply section configures the control circuitry to independently control vapor generation by the first and second vaporizer assemblies.

In some example embodiments, the first vaporizer assembly may include a first dispensing interface configured to draw the first pre-vapor formulation from the first reservoir and a first heater coupled to the first dispensing interface. The first heater may be configured to vaporize the drawn first pre-vapor formulation. The second vaporizer assembly may include a second dispensing interface configured to draw the second pre-vapor formulation from the second reservoir and a second heater coupled to the second dispensing interface. The second heater may be configured to vaporize the drawn second pre-vapor formulation.

BRIEF DESCRIPTION OF THE DRAWINGS

The various features and advantages of the non-limiting embodiments described herein become more apparent upon review of the detailed description in conjunction with the accompanying drawings. The accompanying drawings are merely provided for illustrative purposes and should not be interpreted to limit the scope of the claims. The accompanying drawings are not to be considered as drawn to scale unless explicitly noted. For purposes of clarity, various dimensions of the drawings may have been exaggerated.

FIG. 1A is a side view of an e-vaping device according to some example embodiments.

FIG. 1B is a cross-sectional view along line IB-IB' of the e-vaping device of FIG. 1A.

DETAILED DESCRIPTION OF EXAMPLE EMBODIMENTS

Figure 2:
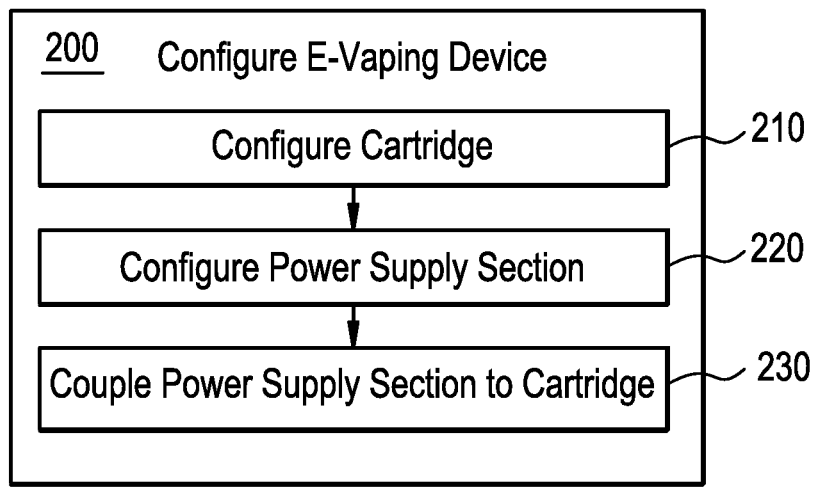
FIG. 2 is a flowchart illustrating a method for configuring an e-vaping device to provide one or more vapors, according to some example embodiments.

Some detailed example embodiments are disclosed herein. However, specific structural and functional details disclosed herein are merely representative for purposes of describing example embodiments. Example embodiments may, however, be embodied in many alternate forms and should not be construed as limited to only the example embodiments set forth herein.

Accordingly, while example embodiments are capable of various modifications and alternative forms, example embodiments thereof are shown by way of example in the drawings and will herein be described in detail. It should be understood, however, that there is no intent to limit example embodiments to the particular forms disclosed, but to the contrary, example embodiments are to cover all modifications, equivalents, and alternatives falling within the scope of example embodiments. Like numbers refer to like elements throughout the description of the figures.

It should be understood that when an element or layer is referred to as being "on," "connected to," "coupled to," or "covering" another element or layer, it may be directly on, connected to, coupled to, or covering the other element or layer or intervening elements or layers may be present. In contrast, when an element is referred to as being "directly on," "directly connected to," or "directly coupled to" another element or layer, there are no intervening elements or layers present. Like numbers refer to like elements throughout the specification. As used herein, the term "and/or" includes any and all combinations of one or more of the associated listed items.

It should be understood that, although the terms first, second, third, etc. may be used herein to describe various elements, regions, layers and/or sections, these elements, regions, layers, and/or sections should not be limited by these terms. These terms are only used to distinguish one element, region, layer, or section from another region, layer, or section. Thus, a first element, region, layer, or section discussed below could be termed a second element, region, layer, or section without departing from the teachings of example embodiments.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various example embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations, and/or elements, but do not preclude the presence or addition of one or more other features, integers, steps, operations, elements, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

FIG. 1A is a side view of an e-vaping device 60 according to some example embodiments. FIG. 1B is a cross-sectional view along line IB-IB' of the e-vaping device of FIG. 1A. The e-vaping device 60 may include one or more of the features set forth in U.S. Patent Application Publication No. 2013/0192623 to Tucker et al. filed Jan. 31, 2013 and U.S. Patent Application Publication No. 2013/0192619 to Tucker et al. filed Jan. 14, 2013, the entire contents of which are incorporated herein by reference thereto. As used herein, the term "e-vaping device" is inclusive of all types of electronic vaping devices, regardless of form, size and/or shape.

Referring to FIG. 1A and FIG. 1B, an e-vaping device 60 includes a replaceable cartridge (or first section) 70 and a reusable power supply section (or second section) 72. Sections 70, 72 are coupled together at complimentary interfaces 74, 84 of the respective sections 70, 72.

In at least some example embodiments, the interfaces 74, 84 may be threaded connectors. However, it should be appreciated that each interface 74, 84 may be any type of connector, including a snug-fit, detent, clamp, bayonet, and/or clasp. One or more of the interfaces 74, 84 may include a cathode connector, anode connector, some combination thereof, etc. to electrically couple one or more elements of the cartridge 70 to one or more power supplies 12 in the power supply section 72 when the interfaces 74, 84 are coupled together. As shown in FIG. 1B, for example, interface 74 includes a connector element 91 configured to electrically couple the vaporizer assemblies 30A, 30B to the power supply 12 when interfaces 74, 84 are coupled together.

As shown in FIG. 1A and FIG. 1B, in some example embodiments, an outlet end insert 20 is positioned at an outlet end of the cartridge 70. The outlet end insert 20 includes at least one outlet port 21 that may be located off-axis from the longitudinal axis of the e-vaping device 60. The at least one outlet port 21 may be angled outwardly in relation to the longitudinal axis of the e-vaping device 60. Multiple outlet ports 21 may be uniformly or substantially uniformly distributed about the perimeter of the outlet end insert 20 so as to uniformly or substantially uniformly distribute a vapor drawn through the at least one outlet port 21 during vaping. Thus, as a vapor is drawn through the at least one outlet port 21, the vapor may move in different directions.

The cartridge 70 includes an outer housing 16 extending in a longitudinal direction and an inner tube (or chimney) 62 coaxially positioned within the outer housing 16. The power supply section 72 includes an outer housing 17 extending in a longitudinal direction. In some example embodiments, the outer housing 16 may be a single tube housing both the cartridge 70 and the power supply section 72 and the entire e-vaping device 60 may be disposable. The outer housings 16, 17 may each have a generally cylindrical cross-section. In some example embodiments, the outer housings 16, 17 may each have a generally and/or substantially triangular cross-section along one or more of the cartridge 70 and the power supply section 72. In some example embodiments, the outer housing 17 may have a greater circumference or dimensions at a tip end than a circumference or dimensions of the outer housing 16 at an outlet end of the e-vaping device 60.

At one end of the inner tube 62, a nose portion of a gasket (or seal) 15 is fitted into an end portion of the inner tube 62. An outer perimeter of the gasket 15 provides at least a partial seal with an interior surface of the outer housing 16. In some example embodiments, the gasket 15 includes conduits extending through the gasket 15 between the outer housing 16 and the inner tube 62. The exterior of the inner tube 62 and the outer housing 16 at least partially define an annular channel 61. One or more conduits through an annular portion of the gasket 18 may assure communication between the annular channel 61 and a space 65 defined between the gasket 15 and a connector element 91. The connector element 91 may be included in the interface 74.

In some example embodiments, a nose portion of another gasket 18 is fitted into another end portion of the inner tube 62. In some example embodiments, the gasket 18 includes conduits extending through the gasket 18 between the outer housing 16 and the inner tube 62. One or more conduits through an annular portion of the gasket 18 may assure communication between the annular channel 61 and an interior 67 of the outlet end insert 20.

In some example embodiments, at least one air inlet port 44 is formed in the outer housing 16, adjacent to the interface 74 to minimize the chance of an adult vaper's fingers occluding one of the ports and to control the resistance-to-draw (RTD) during vaping. In some example embodiments, the air inlet ports 44 may be machined into the outer housing 16 with precision tooling such that their diameters are closely controlled and replicated from one e-vaping device 60 to the next during manufacture.

In a further example embodiment, the air inlet ports 44 may be drilled with carbide drill bits or other high-precision tools and/or techniques. In yet a further example embodiment, the outer housing 16 may be formed of metal or metal alloys such that the size and shape of the air inlet ports 44 may not be altered during manufacturing operations, packaging, and/or vaping. Thus, the air inlet ports 44 may provide consistent RTD. In yet a further example embodiment, the air inlet ports 44 may be sized and configured such that the e-vaping device 60 has a RTD in the range of from about 60 mm $H_2O$ to about 150 mm $H_2O$.

Referring to FIG. 1A and FIG. 1B, the cartridge 70 includes at least a first reservoir 22A and a second reservoir 22B. The space defined between the gaskets 18 and 15 and the inner tube 62 at least partially establishes the confines of the reservoirs 22A, 22B. The space is at least partially partitioned by one or more dividers 23 into multiple separate reservoirs 22A, 22B. The separate reservoirs 22A, 22B may be separate and unconnected reservoirs 22A, 22B. In some example embodiments, the separate reservoirs 22A, 22B are configured to hold different pre-vapor formulations. For example, the separate reservoirs 22A, 22B may include different sets of storage media, where the different sets of storage media are configured to hold different pre-vapor formulations.

As shown in FIG. 1B, the first and second reservoirs 22A, 22B are positioned within the outer housing 16 of the cartridge 70 between opposite ends of the cartridge 70. In the following description, the end of the cartridge 70 at which the outlet end insert 20 is located (the outlet end) is referred to as a first end, and the end at which the interface 74 is located (the tip end) is referred to as the second end. The first end and the second end are opposite ends of the cartridge 70, and the first and second reservoirs 22A, 22B are positioned between the opposite ends.

In the illustrated embodiment, the first and second reservoirs 22A, 22B extend in parallel longitudinally through the cartridge 70, but it will be understood that the disclosure is not limited thereto. For example, in some example embodiments, the first and second reservoirs 22A, 22B extend in parallel orthogonally to a longitudinal axis of the cartridge 70. In some example embodiments, the opposite ends of the respective first and second reservoirs 22A, 22B are aligned along a plane orthogonal to the longitudinal axis of the cartridge 70, but it will be understood that the disclosure is not limited thereto.

The cartridge 70 includes a set of at least first and second vaporizer assemblies 30A, 30B coupled to separate, respective reservoirs 22A, 22B. The first vaporizer assembly 30A is coupled to the first reservoir 22A. The second vaporizer assembly 30B is coupled to the second reservoir 22B. In some embodiments, the e-vaping device 60 may include more than two vaporizer assemblies.

Referring to FIG. 1A and FIG. 1B, the first and second vaporizer assemblies 30A, 30B are coupled to separate, respective reservoirs 22A, 22B on opposite ends of the reservoirs 22A, 22B. For example, the first vaporizer assembly 30A is coupled to the first reservoir 22A on an end of the reservoirs 22A, 22B proximate to the first end. As a result, at least a portion of the first vaporizer assembly 30A extends through the interior 67 of the outlet end insert 20 at the first end of the cartridge 70. In another example, the second vaporizer assembly 30B is coupled to the second reservoir 22B on an end of the reservoirs 22A, 22B proximate to the second end. As a result, at least a portion of the second vaporizer assembly 30B extends through the space 65.

The first and second vaporizer assemblies 30A, 30B are configured to form separate, respective first and second vapors. The first and second vaporizer assemblies 30A, 30B may draw separate pre-vapor formulations from the respective reservoirs 22A, 22B. The first and second vaporizer assemblies 30A, 30B may vaporize the respective drawn pre-vapor formulations to respectively form first and second vapors. First reservoir 22A and second reservoir 22B may hold different pre-vapor formulations, such that the first and second vapors are different respective vapors. The first and second vapors may be formed closer to respective opposite ends of the cartridge 70. Thus, separate vapors may be formed in spatially separated portions of the cartridge 70.

Referring to FIG. 1A and FIG. 1B, the vaporizer assemblies 30A, 30B include separate, respective dispensing interfaces 31A, 31B and heaters 34A, 34B respectively coupled thereto. For example, the first vaporizer assembly 30A includes dispensing interface 31A and a first heater 34A. The first heater 34A is coupled to the dispensing interface 31A. In addition, the second vaporizer assembly 30B includes dispensing interface 31B and a second heater 34B. The second heater 34B is coupled to the dispensing interface 31B.

Dispensing interface 31A is configured to draw at least one pre-vapor formulation from first reservoir 22A. First heater 34A is configured to heat the pre-vapor formulations drawn by the dispensing interface 31A to vaporize the pre-vapor formulations to form a first vapor.

Dispensing interface 31B is configured to draw at least one pre-vapor formulation from second reservoir 22B. Second heater 34B is configured to heat the pre-vapor formulations drawn by the dispensing interface 31B to vaporize the pre-vapor formulations to form a second vapor.

In some example embodiments, at least one of the dispensing interfaces 31A, 31B includes an absorbent material. The absorbent material may be arranged in fluidic communication with the respective heater 34A, 34B coupled to the given at least one dispensing interface 31A, 31B. The absorbent material may include a wick having an elongated form. The wick may be arranged in fluid communication with at least one of the reservoirs 22A, 22B.

In some example embodiments, at least one of the dispensing interfaces 31A, 31B includes a porous material. For example, at least one of the dispensing interfaces 31A, 31B may include at least one ceramic rod configured to direct pre-vapor formulation from at least one of the reservoirs 22A, 22B through an interior of the at least one ceramic rod. In another example, at least one of the dispensing interfaces 31A, 31B may include at least one wick material, that is configured to direct pre-vapor formulation through an interior of the at least one wick material. A wick material may be a flexible wick material.

In some example embodiments, at least one of the dispensing interfaces 31A, 31B includes a nonporous material. For example, at least one of the dispensing interfaces 31A, 31B may include at a channel apparatus that includes a conduit, where the channel apparatus is configured to direct a pre-vapor formulation from at least one of the reservoirs 22A, 22B through the conduit. In another example, at least one of the dispensing interfaces 31A, 31B may include a drip action apparatus. In another example, at least one of the dispensing interfaces 31A, 31B may include a valve configured to direct pre-vapor formulation from at least one of the reservoirs 22A, 22B based on actuation of the valve.

In some example embodiments, at least one of the dispensing interfaces 31A, 31B may include a trunk and one or more roots extending from the trunk. The one or more roots may be multiple roots separately coupled to separate reservoirs, such that the roots extend into the separate reservoirs. For example, as shown in FIG. 1B, dispensing interface 31A includes a trunk 33A and a root 32A. Root 32A extends from the trunk 33A into first reservoir 22A. In addition, as further shown in FIG. 1B, dispensing interface 31B includes a trunk 33B and a root 32B. Root 32B extends from the trunk 33B into second reservoir 22B.

Referring to FIG. 1A and FIG. 1B, the heaters 34A, 34B are coupled to respective dispensing interfaces 31A, 31B at the respective trunks 33A, 33B and may separately vaporize the pre-vapor formulations drawn to the trunks 33A, 33B via the respective roots 32A, 32B, thereby forming separate vapors. For example, first heater 34A is coupled to trunk 33A. First heater 34A may be configured to vaporize pre-vapor formulation drawn to trunk 33A from first reservoir 22A via the root 32A. Second heater 34B is coupled to trunk 33B. Second heater 34B may be configured to vaporize pre-vapor formulation drawn to trunk 33B from second reservoir 22B via the root 32B.

In some example embodiments, one or more of the dispensing interfaces 31A, 31B may include one or more ceramic materials extending into a reservoir. In some example embodiments, one or more of the dispensing interfaces 31A, 31B may include a porous material extending into one or more reservoirs 22A, 22B.

Still referring to FIG. 1A and FIG. 1B, during vaping, a pre-vapor formulation may be transferred from first reservoir 22A via capillary action of the dispensing interface 31A. The pre-vapor formulation may be drawn into the trunk 33A of the dispensing interface 31A. The first heater 34A may at least partially surround a portion of the trunk 33A such that when the first heater 34A is activated, one or more pre-vapor formulations drawn into the trunk 33A may be vaporized by the first heater 34A to form a vapor. In some example embodiments, including the example embodiment illustrated in FIG. 1B, the first heater 34A completely surrounds the trunk 33A.

During vaping, a pre-vapor formulation may be transferred from second reservoir 22B via capillary action of the dispensing interface 31B. The pre-vapor formulation may be drawn into the trunk 33B of the dispensing interface 31B. The second heater 34B may at least partially surround a portion of the trunk 33B such that when the second heater 34B is activated, one or more pre-vapor formulations drawn into the trunk 33B may be vaporized by the second heater 34B to form a vapor. In some example embodiments, including the example embodiment illustrated in FIG. 1B, the second heater 34B completely surrounds the trunk 33B.

As mentioned above with reference to FIG. 1A and FIG. 1B, the first and second vaporizer assemblies 30A, 30B may be configured to form separate, respective first and second vapors proximate to respective, opposite ends of the cartridge 70. For example, as shown in FIG. 1B, the first vaporizer assembly 30A is configured to form a first vapor based on the first heater 34A vaporizing a first pre-vapor formulation drawn to the trunk 33A of the dispensing interface 31A. As further mentioned above, the end of the cartridge 70 at which the outlet end insert 20 is located (the outlet end) is referred to as a first end, and the end at which the interface 74 is located (the tip end) is referred to as the second end. The trunk 33A and the first heater 34A are positioned in the interior 67 proximate to the first end. As a result, because the first vaporizer assembly 30A is coupled to first reservoir 22A on an end of the reservoirs 22A, 22B that is proximate to the first end, the first vapor may be formed closer to the first end than the second end.

In addition, as shown in FIG. 1B, the second vaporizer assembly 30B is configured to form a second vapor based on the second heater 34B vaporizing a second pre-vapor formulation drawn to the trunk 33B of the dispensing interface 31B. The trunk 33B and the second heater 34B are positioned in the space 65 proximate to the second end. As a result, because the second vaporizer assembly 30B is coupled to the second reservoir 22B on an end of the reservoirs 22A, 22B that is proximate to the second end, the second vapor may be formed closer to the second end than the first end.

Because the first and second vapors may be separately, respectively formed closer to the first and second ends of the cartridge 70, the first and second vapors may be formed proximate to opposite ends of the reservoirs 22A, 22B. Therefore, the reservoirs 22A, 22B may be between the locations in the cartridge 70 at which the first and second vapors are formed. The first and second vapors may thus be formed in spatially separated locations in the cartridge 70.

Still referring to FIG. 1A and FIG. 1B, in some example embodiments, the spatially separated first and second vapors may be drawn through the at least one outlet port 21 at different times during vaping, based on the spatial separation of the locations at which the first and second vapors are formed in the cartridge 70. For example, the second vapor may be drawn through the at least one outlet port 21 via passing through the space 65, annular channel 61, and interior 67, while the first vapor may be drawn through the at least one outlet port 21 via interior 67. The second vapor may pass through a longer pathway to be drawn through the at least one outlet port 21, relative to a pathway through which the first vapor may pass to be drawn through at least one outlet port 21. Therefore, where the first and second vapors are formed simultaneously and/or concurrently in the separate, respective spaces 67, 65 during wiping, the first vapor may be drawn through the at least one outlet port 21 before the second vapor is drawn through the at least one outlet port 21, even though the first and second vapors may have been formed simultaneously and/or concurrently.

The spatial separation between the locations at which the first and second vapors are formed may thus cause a temporal separation between the times at which the first and second vapors are drawn through at least one outlet port 21. In some example embodiments, drawing separate vapors through at least one outlet port 21 at different times can provide an enhanced sensory experience. In some example embodiments, the spatial separation of the vapor formation locations may enable temporal separation of the vapor provisions independently of complex circuitry, as the heaters 34A, 34B may be activated simultaneously and/or concurrently rather than according to a complex activation sequence.

Still referring to FIG. 1A and FIG. 1B, in some example embodiments, the cartridge 70 is configured to cause separate vaporizer assemblies 30A, 30B to form separate vapors at separate rates. For example, the vaporizer assemblies 30A, 30B may be configured to cause the heaters 34A, 34B to generate heat at different rates, so that the first and second vapors are formed at different rates. The heaters 34A, 34B may include different materials. One or more electrical circuits included in the e-vaping device 60 may control and/or adjust one or more aspects of electrical power supplied to one or more of the heaters 34A, 34B. An aspect of electrical power so adjusted may include a voltage of electrical power.

Still referring to FIG. 1A and FIG. 1B, the cartridge 70 includes a connector element 91 configured to at least partially establish electrical connections between elements in the cartridge 70 with one or more elements in the power supply section 72. In some example embodiments, the connector element 91 includes an electrode element configured to electrically couple at least one electrical lead to the power supply 12 in the power supply section when interfaces 74, 84 are coupled together. In the example embodiments illustrated in FIG. 1A and FIG. 1B, for example, electrical leads 26-1 and 26-3 are coupled to connector element 91. An electrode element may be one or more of a cathode connector element and an anode connector element. If and/or when interfaces 74, 84 are coupled together, the connector element 91 may be coupled with at least one portion of the power supply 12, as shown in FIG. 1B.

In some example embodiments, one or more of the interfaces 74, 84 include one or more of a cathode connector element and an anode connector element. In the example embodiments illustrated in FIG. 1B, for example, electrical leads 26-2 and 26-4 are coupled to the interface 74. As further shown in FIG. 1B, the power supply section 72 includes a lead 92 that couples the control circuitry 11 to the interface 84. If and/or when interfaces 74, 84 are coupled together, the coupled interfaces 74, 84 may electrically couple leads 26-2 and 26-4 to lead 92.

If and/or when an element in the cartridge 70 is coupled to leads 26-1 and 26-2 or leads 26-3 and 26-4, an electrical circuit through the cartridge 70 and power supply section 72 may be established. The established electrical circuit may include at least the element in the cartridge 70, control circuitry 11, and the power supply 12. The electrical circuit may include lead 92, interfaces 74, 84, and at least one of leads 26-1, 26-2 and leads 26-3, 26-4.

In the example embodiments illustrated in FIG. 1A and FIG. 1B, heater 34A is coupled to interface 74 and connector element 91 via respective leads 26-1 and 26-2, such that the heater 34A may be electrically coupled to the power supply 12 via interface 74 and connector element 91 if and/or when interfaces 74, 84 are coupled together.

In the example embodiments illustrated in FIG. 1A and FIG. 1B, heater 34B is coupled to interface 74 and connector element 91 via respective leads 26-3 and 26-4, such that the heater 34B may be electrically coupled to the power supply 12 via interface 74 and connector element 91 if and/or when interfaces 74, 84 are coupled together.

The control circuitry 11, described further below, is configured to be coupled to the power supply 12, such that the control circuitry 11 may control the supply of electrical power from the power supply 12 to one or more elements of the cartridge 70. The control circuitry 11 may control the supply of electrical power to the element based on controlling the established electrical circuit. For example, the control circuitry 11 may selectively open or close the electrical circuit, adjustably control an electrical current through the circuit, etc.

Still referring to FIG. 1A and FIG. 1B, the power supply section 72 includes a sensor 13 responsive to air drawn into the power supply section 72 via an air inlet port 44a adjacent to a free end or tip end of the e-vaping device 60, a power supply 12, and control circuitry 11. The power supply 12 may include a battery. The sensor 13 may be one or more of a pressure sensor, a microelectromechanical system (MEMS) sensor, etc.

In some example embodiments, the power supply 12 includes a battery arranged in the e-vaping device 60 such that the anode is downstream of the cathode. A connector element 91 contacts the downstream end of the battery. Each heater 34A, 34B is connected to the power supply 12 by respective sets of electrical leads 26-1, 26-2 and 26-3, 26-4, where leads 26-1 and 26-3 are coupled to the connector element 91 and leads 26-2 and 26-4 are coupled to interface 74.

The power supply 12 may be a Lithium-ion battery or one of its variants, for example a Lithium-ion polymer battery. Alternatively, the power supply 12 may be a nickel-metal hydride battery, a nickel cadmium battery, a lithium-manganese battery, a lithium-cobalt battery or a fuel cell. The e-vaping device 60 may be usable by an adult vaper until the energy in the power supply 12 is depleted or in the case of lithium polymer battery, a minimum voltage cut-off level is achieved.

Further, the power supply 12 may be rechargeable and may include circuitry configured to allow the battery to be chargeable by an external charging device. To recharge the e-vaping device 60, a Universal Serial Bus (USB) charger or other suitable charger assembly may be used.

Upon completing the connection between the cartridge 70 and the power supply section 72, the at least one power supply 12 may be electrically connected with the heaters 34A, 34B of the cartridge 70 upon actuation of the sensor 13. Air is drawn primarily into the cartridge 70 through one or more air inlet ports 44. The one or more air inlet ports 44 may be located along the outer housing 16, 17 of the first and second sections 70, 72 or at the coupled interfaces 74, 84.

The sensor 13 may be configured to sense an air pressure drop and initiate application of voltage from the power supply 12 to the heaters 34A, 34B. As shown in the example embodiment illustrated in FIG. 1B, some example embodiments of the power supply section 72 include a heater activation light 48 configured to glow when at least one of the heaters 34A, 34B are activated. The heater activation light 48 may include a light emitting diode (LED). Moreover, the heater activation light 48 may be arranged to be visible to an adult vaper during vaping. In addition, the heater activation light 48 may be utilized for e-vaping system diagnostics or to indicate that recharging is in progress. The heater activation light 48 may also be configured such that the adult vaper may activate and/or deactivate the heater activation light 48 for privacy. As shown in FIG. 1A and FIG. 1B, the heater activation light 48 may be located on the tip end of the e-vaping device 60. In some example embodiments, the heater activation light 48 may be located on a side portion of the outer housing 17.

In addition, the at least one air inlet port 44a is located adjacent to the sensor 13, such that the sensor 13 may sense air flow indicative of vaper being drawn through the outlet end 20, and activate the power supply 12 and the heater activation light 48 to indicate that one or more of the heaters 34A, 34B is working.

Further, the control circuitry 11 may control the supply of electrical power to one or more of the heaters 34A, 34B responsive to the sensor 13. In one example embodiment, the control circuitry 11 may include a maximum, time-period limiter. In another example embodiment, the control circuitry 11 may include a manually operable switch for an adult vaper to initiate vaping. The time-period of the electric current supply to one or more of the heaters 34A, 34B may be pre-set (e.g., prior to controlling the supply of electrical power to one or more of the heaters 34A, 34B) depending on the amount of pre-vapor formulation desired to be vaporized. In some example embodiments, the control circuitry 11 may control the supply of electrical power to one or more of the heaters 34A, 34B as long as the sensor 13 detects a pressure drop.

To control the supply of electrical power to at least one of the heaters 34A, 34B, the control circuitry 11 may execute one or more instances of computer-executable code. The control circuitry 11 may include a processor and a memory. The memory may be a computer-readable storage medium storing computer-executable code.

The control circuitry 11 may include processing circuitry including, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. In some example embodiments, the control circuitry 11 may be at least one of an application-specific integrated circuit (ASIC) and an ASIC chip.

The control circuitry 11 may be configured as a special purpose machine by executing computer-readable program code stored on a storage device. The program code may include program or computer-readable instructions, software elements, software modules, data files, data structures, and/or the like, capable of being implemented by one or more hardware devices, such as one or more of the control circuitry mentioned above. Examples of program code include both machine code produced by a compiler and higher level program code that is executed using an interpreter.

The control circuitry 11 may include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a USB flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The control circuitry 11 may be a special purpose machine configured to execute the computer-executable code to control the supply of electrical power to one or more heaters 34A, 34B. In some example embodiments, an instance of computer-executable code, when executed by the control circuitry 11, causes the control circuitry to control the supply of electrical power to one or more heaters 34A, 34B according to an activation sequence. Controlling the supply of electrical power to one or more heaters 34A, 34B may be referred to herein interchangeably as activating the one or more heaters 34A, 34B.

Still referring to FIG. 1A and FIG. 1B, when at least one of the heaters 34A, 34B is activated, the activated heater of the heaters 34A, 34B may heat a portion of a coupled dispensing interface of the dispensing interfaces 31A, 31B for less than about 10 seconds. Thus, the power cycle (or maximum vaping length) may range from about 2 seconds to about 10 seconds (e.g., about 3 seconds to about 9 seconds, about 4 seconds to about 8 seconds or about 5 seconds to about 7 seconds).

In some example embodiments, the control circuitry 11 of the e-vaping device 60 is configured to independently control the separate heaters 34A, 34B to independently control formation of the first and second vapors. Such independent control may result in controlling the sensory experience provided to an adult vaper.

Still referring to FIG. 1A and FIG. 1B, in some example embodiments, the control circuitry 11 controls the separate heaters 34A, 34B based on controlling the supply of electrical power from the power supply 12 to the separate, respective heaters 34A, 34B. The control circuitry 11 may control the supply of electrical power according to an activation sequence, such that the heaters 34A, 34B are activated and the at least first and second vapors are formed according to the activation sequence. The control circuitry 11 may control the supply of electrical power to heaters 34A, 34B so that both heaters 34A, 34B are activated simultaneously and/or concurrently.

The control circuitry 11 may selectively control the supply of electrical power to heaters 34A, 34B so that the heaters 34A, 34B are activated during separate, at least partially overlapping time periods. The control circuitry 11 may selectively control the supply of electrical power to heaters 34A, 34B so that the heaters 34A, 34B are activated during separate, non-overlapping time periods. In some example embodiments, the control circuitry 11 may selectively control the supply of electrical power to heaters 34A, 34B so that the first and second vapors pass through the at least one outlet port 21 simultaneously and/or concurrently, thereby providing a combined vapor to an adult vapor.

The control circuitry 11 may selectively control the supply of electrical power to heaters 34A, 34B so that the first and second vapors are formed at different times. For example, the control circuitry 11 may control the supply of electrical power to second heater 34B to activate the second heater 34B a certain amount of time prior to supplying electrical power to first heater 34A to activate first heater 34A. The certain amount of time may be associated with a travel time of the second vapor to one or more portions of the interior 67 from the space 65 via channel 61, so that the control circuitry 11 activates the first heater 34A to form the first vapor at about the same tune as the second vapor passes through at least a portion of the interior 67. As a result, the first vapor may be formed in the interior 67 simultaneously and/or concurrently with the second vapor at least partially passing through the interior 67. The first and second vapors may at least partially mix in the interior 67 to form a combined vapor. The combined vapor includes a mixture of the first and second vapors, where the first and second vapors are mixed based on the first and second vapors passing through the at least one outlet port 21 simultaneously and/or concurrently.

In some example embodiments, the control circuitry 11 is configured to independently control the respective rates at which separate vapors are formed in the cartridge 70. For example, the control circuitry 11 may be configured to adjust a voltage of electrical power supplied to one or more of heaters 34A, 34B, so that heaters 34A, 34B generate heat at different rates. The control circuitry 11 may be configured to adjust a voltage of power supplied to one or more of heaters 34A, 34B, so that second heater 34B forms the second vapor at a reduced rate of vapor formation, relative to a rate at which first heater 34A forms the first vapor.

Still referring to FIG. 1A and FIG. 1B, in some example embodiments, the control circuitry 11 may selectively control the supply of electrical power to heaters 34A, 34B of separate vaporizer assemblies 30A, 30B to cause at least one of the vaporizer assemblies 30A, 30B to adjust vapor formation of a separate one of the vaporizer assemblies 30A, 30B. For example, control circuitry 11 may activate second heater 34B prior to activating first heater 34A, such that heat generated by second heater 34B is transferred to at least the first reservoir 22A to which the first vaporizer assembly 30A is coupled. The heat transferred to the first reservoir 22A may be transferred to the first pre-vapor formulation held in the first reservoir 22A, thereby heating the first pre-vapor formulation. Heating the first pre-vapor formulation may cause one or more properties of the first pre-vapor formulation to be changed. For example, a viscosity of the first pre-vapor formulation may be reduced when the first pre-vapor formulation is heated.

Subsequent to heat being transferred to the first reservoir 22A, the control circuitry 11 may activate first heater 34A, and vapor formation by first heater 34A may be adjusted based on the changes in the properties of the first pre-vapor formulation. For example, the first pre-vapor formulation may be drawn through the dispensing interface 31A to the trunk 33A at a faster rate subsequent to the transfer of heat from second heater 34B to first reservoir 22A. In another example, the heated first pre-vapor formulation may be vaporized at a greater rate by first heater 34A based on the transfer of heat. Thus, the control circuitry 11 may control vapor formation by indirectly heating a pre-vapor formulation in a given one of reservoirs 22A, 22B via heat generated by at least one vaporizer assembly 30A, 30B coupled to a separate one of reservoirs 22A, 22B. Such control of vapor formation may control the content of vapors drawn through the at least one outlet port 21 during vaping, thereby enhancing the sensory experience provided by an e-vaping device 60 in which the vaporizer assemblies 30A, 30B and control circuitry 11 are included.

Still referring to FIG. 1A and FIG. 1B, in some example embodiments, at least one of the heaters 34A, 34B may be absent from at least one of vaporizer assemblies 30A, 30B such that the at least one of the vaporizer assemblies 30A, 30B is configured to form a vapor based on heat generated at another one of the vaporizer assemblies 30A, 30B. For example, second heater 34B may be absent from dispensing interface 31B. The second vaporizer assembly 30B may be configured to generate a vapor based on a vapor generated by the first vaporizer assembly 30A passing in flow communication with the dispensing interface 31B. The vapor generated by the first vaporizer assembly 30A may retain heat generated by the first heater 34A included in the first vaporizer assembly 30A. The vapor generated by the first vaporizer assembly 30A may transfer at least some heat to the dispensing interface 31B, thereby causing a pre-vapor formulation held by the dispensing interface 31B to vaporize. In some example embodiments, the vapor generated by the first vaporizer assembly 30A may remove (e.g., elute) one or more elements of a pre-vapor formulation from the dispensing interface 31B.

A pre-vapor formulation, as described herein, is a material or combination of materials that may be transformed into a vapor. For example, the pre-vapor formulation may be a liquid, solid and/or gel formulation including, but not limited to, water, beads, solvents, active ingredients, ethanol, plant extracts, natural or artificial flavors, and/or pre-vapor formulations such as glycerin and propylene glycol. Different pre-vapor formulations may include different elements. Different pre-vapor formulations may have different properties. For example, different pre-vapor formulations may have different viscosities when the different pre-vapor formulations are at a common temperature. The pre-vapor formulation may include those described in U.S. Patent Application Publication No. 2015/0020823 to Lipowicz et al. filed Jul. 16, 2014 and U.S. Patent Application Publication No. 2015/0313275 to Anderson et al. filed Jan. 21, 2015, the entire contents of each of which is incorporated herein by reference thereto.

The pre-vapor formulation may include nicotine or may exclude nicotine. The pre-vapor formulation may include one or more tobacco flavors. The pre-vapor formulation may include one or more flavors that are separate from one or more tobacco flavors.

In some example embodiments, a pre-vapor formulation that includes nicotine may also include one or more acids. The one or more acids may be at least one of pyruvic acid, formic acid, oxalic acid, glycolic acid, acetic acid, isovaleric acid, valeric acid, propionic acid, octanoic acid, lactic acid, levulinic acid, sorbic acid, malic acid, tartaric acid, succinic acid, citric acid, benzoic acid, oleic acid, aconitic acid, butyric acid, cinnamic acid, decanoic acid, 3,7-dimethyl-6-octenoic acid, 1-glutamic acid, heptanoic acid, hexanoic acid, 3-hexenoic acid, trans-2-hexenoic acid, isobutyric acid, lauric acid, 2-methylbutyric acid, 2-methylvaleric acid, myristic acid, nonanoic acid, palmitic acid, 4-penenoic acid, phenylacetic acid, 3-phenylpropionic acid, hydrochloric acid, phosphoric acid, sulfuric acid and combinations thereof.

At least one of the reservoirs 22A, 22B may include a pre-vapor formulation, and optionally a storage medium configured to store the pre-vapor formulation therein. The storage medium may include a winding of cotton gauze or other fibrous material about a portion of the cartridge 70.

The storage medium of one or more reservoirs 22A, 22B may be a fibrous material including at least one of cotton, polyethylene, polyester, rayon and combinations thereof. The fibers may have a diameter ranging in size from about 6 microns to about 15 microns (e.g., about 8 microns to about 12 microns or about 9 microns to about 11 microns). The storage medium may be a sintered, porous or foamed material. Also, the fibers may be sized to be irrespirable and may have a cross-section that has a Y-shape, cross shape, clover shape or any other suitable shape. In some example embodiments, one or more reservoirs 22A, 22B may include a filled tank lacking any storage medium and containing only pre-vapor formulation.

At least one of the reservoirs 22A, 22B may be sized and configured to hold enough pre-vapor formulation such that the e-vaping device 60 may be configured for vaping for at least about 200 seconds. The e-vaping device 60 may be configured to allow each vaping to last a maximum of about 5 seconds.

At least one of the dispensing interfaces 31A, 31B may include filaments (or threads) having a capacity to draw one or more pre-vapor formulations. For example, at least one of the dispensing interfaces 31A, 31B may be a bundle of glass (or ceramic) filaments, a bundle including a group of windings of glass filaments, etc., all of which arrangements may be capable of drawing pre-vapor formulation via capillary action by interstitial spacings between the filaments. The filaments may be generally aligned in a direction perpendicular (transverse) to the longitudinal direction of the e-vaping device 60. In some example embodiments, the wick may include one to eight filament strands, each strand comprising a plurality of glass filaments twisted together. The end portions of at least one of the dispensing interfaces 31A, 31B may be flexible and foldable into the confines of one or more reservoirs 22A, 22B. The filaments may have a cross-section that is generally cross-shaped, clover-shaped, Y-shaped, or in any other suitable shape. In some example embodiments, at least one of the dispensing interfaces 31A, 31B includes multiple separate wicks coupled together. The coupled portions of the wicks may establish a trunk of a dispensing interface, and the non-coupled portions of the wicks extending away from the trunk may be one or more roots of a dispensing interface.

A dispensing interface may include any suitable material or combination of materials, also referred to herein as wicking materials. Examples of suitable materials may be, but not limited to, glass, ceramic- or graphite-based materials. A dispensing interface may have any suitable capillarity drawing action to accommodate pre-vapor formulations having different physical properties such as density, viscosity, surface tension and vapor pressure.

In some example embodiments, at least one of the heaters 34A, 34B may include a wire coil that at least partially surrounds a trunk 33A, 33B of at least one dispensing interface 31A, 31B. The wire may be a metal wire and/or the wire coil may extend fully or partially along the length of the trunk 33A, 33B. A wire coil may further extend fully or partially around the circumference of the trunk 33A, 33B. In some example embodiments, a wire coil may or may not be in contact with a dispensing interface 31A, 31B to which the wire coil is coupled.

In the example embodiment illustrated in FIG. 1B, the trunks 33A, 33B of dispensing interfaces 31A, 31B are oriented transverse to a longitudinal axis of the cartridge 70. The roots 32A, 32B of the dispensing interfaces 31A, 31B are extending in parallel to the longitudinal axis of the cartridge 70 in the example embodiment illustrated in FIG. 1B. In some example embodiments, the trunk of one or more of the dispensing interfaces 31A, 31B may extend in parallel with the longitudinal axis of the cartridge 70. In some example embodiments, a dispensing interface having a trunk that extends in parallel with a longitudinal axis of the cartridge 70 may be configured to provide improved delivery of pre-vapor formulation from a reservoir to the trunk and thus improved vaporization of the pre-vapor formulation. In some example embodiments, a dispensing interface trunk that extends in parallel with the longitudinal axis of the cartridge 70 may have improved exposure to air drawn through the cartridge 70 during vaping, thereby improving the amount of vapor drawn into the airstream during vaping.

At least one of the heaters 34A, 34B may be formed of any suitable electrically resistive materials. Examples of suitable electrically resistive materials may include, but not limited to, titanium, zirconium, tantalum and metals from the platinum group. Examples of suitable metal alloys include, but not limited to, stainless steel, nickel, cobalt, chromium, aluminum-titanium-zirconium, hafnium, niobium, molybdenum, tantalum, tungsten, tin, gallium, manganese and iron-containing alloys, and super-alloys based on nickel, iron, cobalt, stainless steel. For example, at least one of the heaters 34A, 34B may be formed of nickel aluminide, a material with a layer of alumina on the surface, iron aluminide and other composite materials, the electrically resistive material may optionally be embedded in, encapsulated or coated with an insulating material or vice-versa, depending on the kinetics of energy transfer and the external physicochemical properties required. At least one of the heaters 34A, 34B may include at least one material selected from the group including at least one of stainless steel, copper, copper alloys, nickel-chromium alloys, super alloys and combinations thereof. In some example embodiments, at least one of the heaters 34A, 34B may be formed of nickel-chromium alloys or iron-chromium alloys. In some example embodiments, at least one of the heaters 34A, 34B may be a ceramic heater having an electrically resistive layer on an outside surface thereof.

At least one of the heaters 34A, 34B may heat one or more pre-vapor formulations in at least one of the dispensing interfaces 31A, 31B by thermal conduction. Alternatively, heat from at least one of the heaters 34A, 34B may be conducted to the one or more pre-vapor formulations by a heat conductive element or the at least one of the heaters 34A, 34B may transfer heat to the incoming ambient air that is drawn through the e-vaping device 60 during vaping, which in turn heats the pre-vapor formulation by convection.

In some example embodiments, e-vaping device 60 includes more than two vaporizer assemblies, where the vaporizer assemblies are configured to separately form separate, respective vapors.

In some example embodiments, the cartridge 70 may be replaceable. In other words, once the pre-vapor formulation of the cartridge 70 is depleted, only the cartridge 70 may be replaced. An alternate arrangement may include an example embodiment where the entire e-vaping device 60 may be disposed once one or more of the reservoirs 22A, 22B are depleted.

In an example embodiment, the e-vaping device 60 may be about 80 mm to about 110 mm long and about 7 mm to about 8 mm in diameter. For example, in one example embodiment, the e-vaping device may be about 84 mm long and may have a diameter of about 7.8 mm.

FIG. 2 is a flowchart illustrating a method for configuring an e-vaping device to provide one or more vapors, according to some example embodiments. The configuring may be implemented with regard to any of the embodiments of e-vaping devices included herein. In some example embodiments, one or more portions of the configuring are implemented by a configuror. The configuror may be one or more of a human operator, a machine, some combination thereof, etc. The machine may be a fabrication machine. The machine may be a special purpose machine configured to implement the configuring based on executing program code stored in a memory device.

Referring to FIG. 2, at 210, the configuror configures a cartridge (or first section) to form separate vapors at separate ends of the cartridge. Such configuring includes configuring elements of the cartridge as shown with regard to the cartridge 70 in FIG. 1A and FIG. 1B. Such configuring is discussed in further detail below with regard to FIG. 3.

At 220, the configuror configures a power supply section (or second section) to provide electrical power. The configuring of the power supply section may include one or more of installing a power supply in the power supply section, charging a power supply in the power supply section, coupling control circuitry to the power supply section, etc.

At 230, the configuror couples the cartridge and power supply section at complimentary interfaces, such that the power supply in the power supply section is electrically coupled to heaters included at separate ends of the cartridge and may be operated to cause the heaters to heat separate pre-vapor formulations drawn to the separate ends of the cartridge.

In some example embodiments, the cartridge may be replaced with a different cartridge, and the different cartridge may include a different set of pre-vapor formulations.

Figure 3:
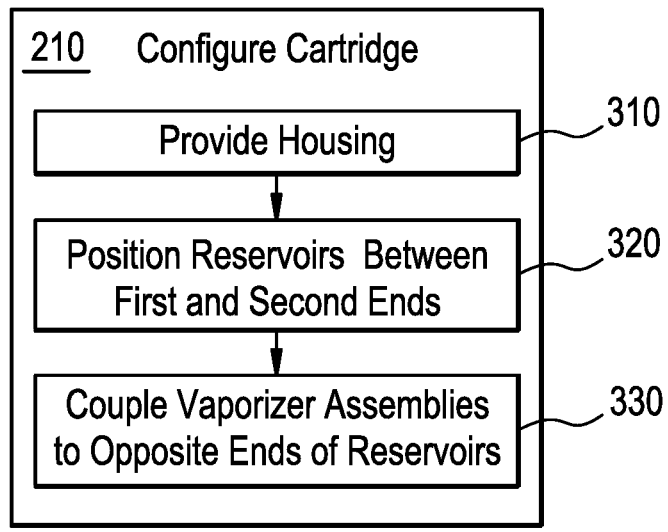
FIG. 3 is a flowchart illustrating a method for configuring a cartridge, according to some example embodiments.

FIG. 3 is a flowchart illustrating a method for configuring a cartridge, according to some example embodiments. The configuring 210 may be implemented with regard to any of the embodiments of cartridges included herein. Such configuring includes configuring elements of a cartridge as shown with regard to the cartridge 70 in FIG. 1A and FIG. 1B. The configuring may be implemented with regard to any of the embodiments of e-vaping devices included herein. In some example embodiments, one or more portions of the configuring are implemented by a configuror. The configuror may be one or more of a human operator, a machine, some combination thereof, etc. The machine may be a fabrication machine. The machine may be a special purpose machine configured to implement the configuring based on executing program code stored in a memory device.

Referring to FIG. 3, at 310, the configuror provides a housing. The housing may include an enclosure and an opening at one end of the enclosure.

At 320, the configuror positions multiple reservoirs within the enclosure of the cartridge, between separate ends of the enclosure. The reservoirs may be bound by separate housings. The reservoirs may be provided via partitioning a portion of the enclosure within the housing.

At 330, the configuror couples separate vaporizer assemblies to separate, respective sets of one or more reservoirs proximate to separate ends of the cartridge housing interior, such that the vaporizer assemblies are configured to draw separate pre-vaping formulations from separate reservoirs to separate ends of the enclosure and vaporize the separate pre-vapor formulations at the separate ends. Each vaporizer assembly may include a dispensing interface coupled a set of reservoirs in the enclosure of the cartridge. Coupling the dispensing interface to the set of reservoirs may include coupling the dispensing interface to portions of the cartridge and extending separate roots of the dispensing interface into separate reservoirs via the portions of the cartridge. In some example embodiments, the dispensing interface is coupled to a gasket, where the gasket seals one end of the reservoirs, so that the separate roots of the dispensing interface extend into the separate reservoirs through an interior of the gasket. Each vaporizer assembly may include a heater coupled to a dispensing interface. Each heater may be coupled to a power supply section interface of the cartridge via one or more sets of electrical leads, so that the heaters may receive electrical power from a power supply coupled to the power supply section interface.

While a number of example embodiments have been disclosed herein, it should be understood that other variations array be possible. Such variations are not to be regarded as a departure from the spirit and scope of the present disclosure, and all such modifications as would be obvious to one skilled in the art are intended to be included within the scope of the following claims.

We claim:

1. A cartridge for an e-vaping device, the cartridge comprising:
   a housing including first and second ends;
   at least first and second reservoirs positioned within the housing between the first and second ends, the first and second reservoirs extending in parallel longitudinally between the first and second ends of the housing, the first and second reservoirs being configured to hold respective first and second pre-vapor formulations;
   a first gasket defining a first end of the first and second reservoirs, the first gasket and the first end of the housing defining a first space within the housing;
   a second gasket defining a second end of the first and second reservoirs, the second gasket and the second end of the housing defining a second space within the housing; and
   at least first and second vaporizer assemblies positioned within the housing on opposite ends of the first and second reservoirs, the first vaporizer assembly being coupled to the first reservoir and extending into the first space between the first and second reservoirs and the first end of the housing, the first vaporizer assembly being configured to vaporize the first pre-vapor formulation to generate a first vapor in the first space, the second vaporizer assembly being coupled to the second reservoir and extending into the second space between the first and second reservoirs and the first end of the housing, the second vaporizer assembly being configured to vaporize the second pre-vapor formulation to generate a second vapor in the second space; and
   at least one electrode electrically coupled to the first and second vaporizer assemblies via separate, respective electrical leads.

2. The cartridge of claim 1, wherein
   the first vaporizer assembly includes,
      a first dispensing interface configured to draw the first pre-vapor formulation from the first reservoir, and
      a first heater coupled to the first dispensing interface, the first heater being configured to vaporize the drawn first pre-vapor formulation; and
   the second vaporizer assembly includes,
      a second dispensing interface configured to draw the second pre-vapor formulation from the second reservoir, and
      a second heater coupled to the second dispensing interface, the second heater being configured to vaporize the drawn second pre-vapor formulation.

3. The cartridge of claim 2, wherein the first dispensing interface includes a porous material, the porous material being arranged in fluidic communication with the first heater.

4. The cartridge of claim 3, wherein the porous material is a wick having an elongated form and arranged in fluidic communication with the first reservoir.

5. The cartridge of claim 4, wherein the wick extends at least partially through the first heater.

6. The cartridge of claim 2, wherein the first and second heaters include different materials.

7. An e-vaping device, comprising:
   a cartridge, the cartridge including,
      a housing including first and second ends;
      at least first and second reservoirs positioned within the housing between the first and second ends, the first and second reservoirs extending in parallel longitudinally between the first and second ends of the housing, the first and second reservoirs being configured to hold respective first and second pre-vapor formulations;
      a first gasket defining a first end of the first and second reservoirs, the first gasket and the first end of the housing defining a first space within the housing;
      a second gasket defining a second end of the first and second reservoirs, the second gasket and the second end of the housing defining a second space within the housing; and
      at least first and second vaporizer assemblies positioned within the housing on opposite ends of the first and second reservoirs, the first vaporizer assembly being coupled to the first reservoir and extending into the first space between the first and second reservoirs and the first end of the housing, the first vaporizer assembly being configured to vaporize the first pre-vapor formulation to generate a first vapor in the first space, the second vaporizer assembly being coupled to the second reservoir and extending into the second space between the first and second reservoirs and the first end of the housing, the second vaporizer assembly being configured to vaporize the second pre-vapor formulation to generate a second vapor in the second space; and
   a power supply section configured to selectively supply power to the first and second vaporizer assemblies.

8. The e-vaping device of claim 7, wherein the power supply section further includes control circuitry, the control circuitry being configured to independently control vapor generation by the first and second vaporizer assemblies.

9. The e-vaping device of claim 7, wherein
the first vaporizer assembly includes,
a first dispensing interface configured to draw the first pre-vapor formulation from the first reservoir, and
a first heater coupled to the first dispensing interface, the first heater being configured to vaporize the drawn first pre-vapor formulation; and
the second vaporizer assembly includes,
a second dispensing interface configured to draw the second pre-vapor formulation from the second reservoir, and
a second heater coupled to the second dispensing interface, the second heater being configured to vaporize the drawn second pre-vapor formulation.

10. The e-vaping device of claim 9, wherein the first dispensing interface includes a porous material, the porous material being arranged in fluidic communication with the first heater.

11. The e-vaping device of claim 10, wherein the porous material is a wick having an elongated form and arranged in fluidic communication with the first reservoir.

12. The e-vaping device of claim 7, wherein the power supply section includes a rechargeable battery, the power supply section being removably coupled to the cartridge.

13. A method, comprising:
configuring a cartridge to generate separate vapors at separate ends of an enclosure, the configuring including,
positioning at least first and second reservoirs in a housing, such that the first and second reservoirs are positioned between first and second ends of the housing and extend in parallel longitudinally between the first and second ends of the housing, the first and second reservoirs being configured to hold respective first and second pre-vapor formulations, the positioning including providing a first gasket defining a first end of the first and second reservoirs, the first gasket and the first end of the housing defining a first space within the housing, the positioning further including providing a second gasket defining a second end of the first and second reservoirs, the second gasket and the second end of the housing defining a second space within the housing; and coupling at least first and second vaporizer assemblies to opposite ends of the first and second reservoirs, such that
the first vaporizer assembly is coupled to the first reservoir and extends into the first space between the first and second reservoirs and the first end of the housing, and the first vaporizer assembly is configured to vaporize the first pre-vapor formulation to generate a first vapor in the first space, and
the second vaporizer assembly is coupled to the second reservoir and extending into the second space between the first and second reservoirs and the first end of the housing, and the second vaporizer assembly is configured to vaporize the second pre-vapor formulation to generate a second vapor in the second space.

14. The method of claim 13, further comprising:
coupling the cartridge to a power supply section, such that the power supply section is configured to selectively supply power to the first and second vaporizer assemblies.

15. The method of claim 14, wherein the power supply section includes control circuitry, the control circuitry being configured to control power supplied from the power supply section, such that coupling the cartridge to the power supply section configures the control circuitry to independently control vapor generation by the first and second vaporizer assemblies.

16. The method of claim 13, wherein
the first vaporizer assembly includes,
a first dispensing interface configured to draw the first pre-vapor formulation from the first reservoir, and
a first heater coupled to the first dispensing interface, the first heater being configured to vaporize the drawn first pre-vapor formulation; and
the second vaporizer assembly includes,
a second dispensing interface configured to draw the second pre-vapor formulation from the second reservoir, and
a second heater coupled to the second dispensing interface, the second heater being configured to vaporize the drawn second pre-vapor formulation.

\* \* \* \* \*